(12) United States Patent
Unay et al.

(10) Patent No.: US 9,495,388 B2
(45) Date of Patent: Nov. 15, 2016

(54) VISUALIZATION OF RELEVANCE FOR CONTENT-BASED IMAGE RETRIEVAL

(75) Inventors: Devrim Unay, Istanbul (TR); Ahmet Ekin, Eindhoven (NL)

(73) Assignee: Koninkijke Philips N.V., Eindhoven (NL)

( * ) Notice: Subject to any disclaimer, the term of this patent is extended or adjusted under 35 U.S.C. 154(b) by 28 days.

(21) Appl. No.: 13/392,113

(22) PCT Filed: Aug. 30, 2010

(86) PCT No.: PCT/IB2010/053872
§ 371 (c)(1),
(2), (4) Date: Feb. 24, 2012

(87) PCT Pub. No.: WO2011/027275
PCT Pub. Date: Mar. 10, 2011

(65) Prior Publication Data
US 2012/0158717 A1    Jun. 21, 2012

(30) Foreign Application Priority Data
Sep. 4, 2009  (EP) .................................. 09169495

(51) Int. Cl.
*G06F 17/30* (2006.01)
*G06F 19/00* (2011.01)

(52) U.S. Cl.
CPC ... *G06F 17/30277* (2013.01); *G06F 17/30244* (2013.01); *G06F 19/321* (2013.01)

(58) Field of Classification Search
CPC ............... G06F 17/30244; G06F 17/30247; G06F 19/321; G06F 19/322; G06F 17/30864; G06F 17/30867; G06F 17/3025
See application file for complete search history.

(56) References Cited

U.S. PATENT DOCUMENTS 5,764,792 A  *  6/1998  Kennealy ...................... 382/133
6,584,221 B1     6/2003  Moghaddam et al.
(Continued)

FOREIGN PATENT DOCUMENTS

CN    101359285 A    2/2009
JP    2001134765 A   5/2001
(Continued)

OTHER PUBLICATIONS

Sorgel et al, "Computer Aided Diagnosis of Bone Lesions in the Facial Skeleton", Proc. Workshop: Image Proc. in Medicine, Mar. 1998, pp. 179-183.
(Continued)

*Primary Examiner* — Leslie Wong

(57) ABSTRACT

A system (100) includes a retrieval unit (110) for retrieving an image from the storage of images, on the basis of the similarity of images from the storage of images to a query image. The similarity is defined by means of a similarity function. A relevance unit (120) computes the relevance of a first portion of the retrieved image to a respective first portion of the query image and of a second portion of the retrieved image to the respective second portion of the query image. A visualization unit (130) visualizes the relevance of the first and second portion of the retrieved image to the respective first and second portion of the query image. The relevance of the first and second portion of the retrieved image to the respective first and second portion of the query image is computed using a first and second relevance function. The computed values of the relevance are visualized, e.g. using a color coding and coloring the first and second portion of each retrieved image. The colored portions are easy to see and analyze. Thus, the system facilitates visualizing and comparing retrieved images with respect to each other as well as with the query image.

14 Claims, 5 Drawing Sheets

(56) References Cited

U.S. PATENT DOCUMENTS

| | | | |
|---|---|---|---|
| 6,804,683 B1* | 10/2004 | Matsuzaki et al. | |
| 6,937,761 B2* | 8/2005 | Thomas et al. | 382/173 |
| 7,478,091 B2* | 1/2009 | Mojsilovic et al. | |
| 7,646,898 B1* | 1/2010 | Nowinski et al. | 382/128 |
| 7,840,076 B2* | 11/2010 | Bouguet et al. | 382/224 |
| 7,933,440 B2* | 4/2011 | Littmann | 382/131 |
| 8,218,835 B2* | 7/2012 | Matsuda et al. | 382/128 |
| 2002/0136468 A1 | 9/2002 | Sun | |
| 2003/0006770 A1* | 1/2003 | Smith | 324/309 |
| 2003/0095147 A1* | 5/2003 | Daw | 345/771 |
| 2003/0214290 A1* | 11/2003 | van Muiswinkel et al. | 324/307 |
| 2004/0103093 A1* | 5/2004 | Furuhashi et al. | 707/3 |
| 2008/0103834 A1* | 5/2008 | Reiner | 705/3 |
| 2008/0215630 A1* | 9/2008 | Oosawa | G06F 19/3443 |
| 2008/0267452 A1* | 10/2008 | Kondo et al. | 382/103 |
| 2009/0028403 A1* | 1/2009 | Bar-Aviv et al. | 382/128 |
| 2009/0070378 A1* | 3/2009 | Cho et al. | 707/104.1 |
| 2009/0290772 A1* | 11/2009 | Avinash et al. | 382/130 |
| 2010/0259263 A1* | 10/2010 | Holland et al. | 324/310 |
| 2011/0105881 A1* | 5/2011 | Kakimoto et al. | 600/407 |
| 2011/0254859 A1* | 10/2011 | Matsuda | 345/633 |
| 2011/0268328 A1* | 11/2011 | Bar-Aviv et al. | 382/128 |
| 2012/0283114 A1* | 11/2012 | Cohen et al. | 506/9 |

FOREIGN PATENT DOCUMENTS

| | | | |
|---|---|---|---|
| JP | 2002245048 A | 8/2001 | |
| JP | 20020007413 A | 1/2002 | |
| JP | 2004240751 A | 8/2004 | |
| JP | 2008192011 A | 8/2008 | |
| JP | 2009086762 A | 4/2009 | |

OTHER PUBLICATIONS

Xue et al, "Investigating CBIR Techniques for Cervicographic Images", Proceedings of American Medical Informatics Association Annual Symposium, 2007, pp. 826-830.

Akgul et al, "Automated Diagnosis of Alzheimer's Disease Using Image Similarity and User Feedback", Proc. of ACM International Conference on Image and Video Retrieval (CIVR), 2009, 8 Pages.

Jing et al, "Pagerank for Product Image Search", WWW 2008/ Refereed Track: Rich Media, Apr. 21-25, 2008, pp. 307-315.

Viitaniemi et al, "Focusing Keywords to Automatically Extracted Image Segments Using Self-Organising Maps", From http://www.cis.hut.fi/projects/cbir/papers/scip2006.pdf, 2006, pp. 1-34.

Datta et al, "Image Retrieval: Ideas, Influences, and Trends of the New Age", ACM Computing Surveys, vol. 40, No. 2, Article 5, 2008, p. 5:1-5:60.

Rui et al, "Relevance Feedback: A Power Tool for Interactive Content-Based Image Retrieval", IEEE Transactions on Circuits and Video Technology, vol. 6, Sep. 1998, pp. 644-655.

\* cited by examiner

VISUALIZATION OF RELEVANCE FOR CONTENT-BASED IMAGE RETRIEVAL

FIELD OF THE INVENTION

The invention relates to content-based image retrieval and, more particularly, to visualizing content-based image retrieval.

BACKGROUND OF THE INVENTION

Content-based information retrieval (CBIR) attempts to solve the problem of searching for digital images in large databases. One of the concerns in CBIR literature is about how to rank the results of these similarity searches, and how to visualize that ranking There exist many different ways in which a digital image can be "similar" to a query image. A CBIR system should make the user aware of the similarity definition and how to interpret the relationship between the retrieved images and the query. Typically, the retrieved images are ranked based on their similarity to the query image. The system is arranged to show the retrieved images to the user in a sequential order, the more similar images preceding those less similar. Several examples of CBIR systems are described in a review article by R. Datta et al entitled "Image retrieval, ideas, influences and trends of the new age", published in ACM Computing Surveys 40, No. 2 pp. 5:1-60, 2008.

A drawback of the existing CBIR methods is that the user is often not able to see why the retrieved images are similar or dissimilar to the query image. In particular, it is often not obvious whether a suspicious portion of interest of the query image is similar to the respective portion of the retrieved image. It also difficult to compare and evaluate retrieved images with respect to each other.

SUMMARY OF THE INVENTION

It would be advantageous to provide a CBIR system which facilitates comparing retrieved images with respect to each other as well as with the query image.

Thus, in an aspect, the invention provides a system for retrieving an image from the storage of images, the system comprising:
- a retrieval unit for retrieving an image from the storage of images, on the basis of similarity of images from the storage of images to a query image, wherein the similarity is defined by means of a similarity function;
- a relevance unit for computing relevance of a first portion of the retrieved image to a respective first portion of the query image and of a second portion of the retrieved image to a respective second portion of the query image; and
- a visualization unit for visualizing the relevance of the first and second portion of the retrieved image to the respective first and second portion of the query image.

The relevance of the first and second portion of the retrieved image to the respective first and second portion of the query image may be computed using a first and second relevance function. The computed values of the relevance may be visualized, e.g. using a color coding and coloring the first and second portion of each retrieved image. The colored portions are easy to see and analyze. Thus, the system of the invention facilitates visualizing and comparing retrieved images with respect to each other as well as with the query image In an embodiment, the system further comprises a portion unit for determining the first and/or second portion of the query image. The first and/or second portion of the query image may be based on a user input. The user input may comprise control points for defining a closed contour comprising pixels of the first or second portion of the query image. In another embodiment the query image may be partitioned into a plurality of parts and the user may indicate the parts comprised in the first and/or second portion of the query image, using a mouse pointer, for example. This allows the user to define the important regions of the image.

In an embodiment of the system, the portion unit is adapted for segmenting the query image, and the first and/or second portion of the query image is determined on the basis of said segmentation of the query image. This allows determining the first and/or second portion of the query image, based on image features, representing, for example, anatomic features of an imaged body part of a patient.

In an embodiment, the system further comprises a rank unit for determining the rank of the retrieved image, and the rank is determined based on the similarity of the retrieved image to the query image and/or on the relevance of the first and second portion of the retrieved image to the respective first and second portion of the query image. The rank unit may be adapted to employ various approaches. In an embodiment, the relevance of the first portion is considered more important than the relevance of the second portion. The rank is a weighted sum of the first and second portion relevance. The relevance of the more important first portion has higher weight.

In an embodiment of the system, the retrieval unit is adapted for registering images from the storage of images with the query image. This makes computing image similarities and the relevance of the first and second image portion simpler. Also, this simplifies determining the first and second portion of the retrieved image, based on the first and second portion of the query image; for example, the pixel or voxel coordinates of the portions of the retrieved image registered with the query image may be identical with the respective pixel or voxel coordinates of the portions of the query image.

In an embodiment, the system further comprises an update unit for updating the similarity function on the basis of the computed values of relevance of the first and second portion of the retrieved image. Methods of updating the similarity function based on relevance feedback are known, e.g. from the paper by Rui et al. "Relevance Feedback: A Power Tool for Interactive Content-Based Image Retrieval" (IEEE Transaction on Circuits and System for Video Technology, vol. 6 September 1998, pp. 644-655) or from Akgul et al. "Automated Diagnosis of Alzheimer's Disease using Image Similarity and User Feedback" (Proc. of ACM International Conference on Image and Video Retrieval (CIVR), Santorini, Greece, 2009). Using an updated similarity function may improve the image retrieval. In particular, the updated similarity function may be arranged to favor images whose first and second portion are similar to the respective first and second portion of the query image.

In an embodiment, the system further comprises a feedback unit for receiving a user feedback on the relevance of the first and second portion of the retrieved image to the respective first and second portion of the query image, and the update unit is adapted to use the user feedback for updating the similarity function. For example, the user may indicate whether the computed relevance of the first or second portion of the retrieved image to the respective first or second portion of the query image is meaningful or not.

If the relevance is indicated as meaningful, a term contributing to that relevance value may be included in the similarity function to retrieve images having the first or second portion similar to the respective first or second portion of the query image.

In an embodiment of the system, the relevance of the first and second portion of the retrieved image to the respective first and second portion of the query image is computed using the similarity function. The similarity function may comprise a sum of terms for computing the similarity of portions of a retrieved image to the respective portions of the query image. The computed similarity of the first and second portion of the retrieved image to the respective first and second portion of the query image may be used as the relevance of the first and second portion of the retrieved image to the respective first and second portion of the query image.

In an embodiment of the system, the visualization unit is adapted for indicating the computed relevance of a first portion of the retrieved image to a respective first portion of the query image and of a second portion of the retrieved image to a respective second portion of the query image using color coding, and wherein the user can select the color and/or transparency of the coding. Thus, the user can see the first and second portion relevance score with minimum obstruction to the image detail.

In a further aspect, the system according to the invention is comprised in a database system. The system of the invention improves the database visualization functions.

In a further aspect, the system according to the invention is comprised in an image acquisition apparatus.

In a further aspect, the system according to the invention is comprised in a workstation.

In a further aspect, the invention provides a method of retrieving an image from the storage of images, the method comprising:
- a retrieval step for retrieving an image from the storage of images, on the basis of similarity of images from the storage of images to a query image, wherein the similarity is defined by means of a similarity function;
- a relevance step for computing relevance of a first portion of the retrieved image to a respective first portion of the query image and of a second portion of the retrieved image to a respective second portion of the query image; and
- a visualization step for visualizing the relevance of the first and second portion of the retrieved image to the respective first and second portion of the query image.

In a further aspect, the invention provides a computer program product to be loaded by a computer arrangement, the computer program comprising instructions for retrieving an image from the storage of images, the computer arrangement comprising a processing unit and a memory, the computer program product, after being loaded, providing said processing unit with the capability to carry out steps of the method.

It will be appreciated by those skilled in the art that two or more of the above-mentioned embodiments, implementations, and/or aspects of the invention may be combined in any way deemed useful.

Modifications and variations of the system, of the database, of the image acquisition apparatus, of the workstation, of the method, and/or of the computer program product, which correspond to the described modifications and variations of the system or the method, can be carried out by a person skilled in the art on the basis of the present description.

A person skilled in the art will appreciate that the method may be applied to multidimensional image data, e.g., 2-dimensional (2-D), 3-dimensional (3-D) or 4-dimensional (4-D) image data, acquired by various acquisition modalities such as, but not limited to, X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The invention is defined by the independent claims. Advantageous embodiments are defined in the dependent claims.

BRIEF DESCRIPTION OF THE DRAWINGS

These and other aspects of the invention will become apparent from and will be elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1:
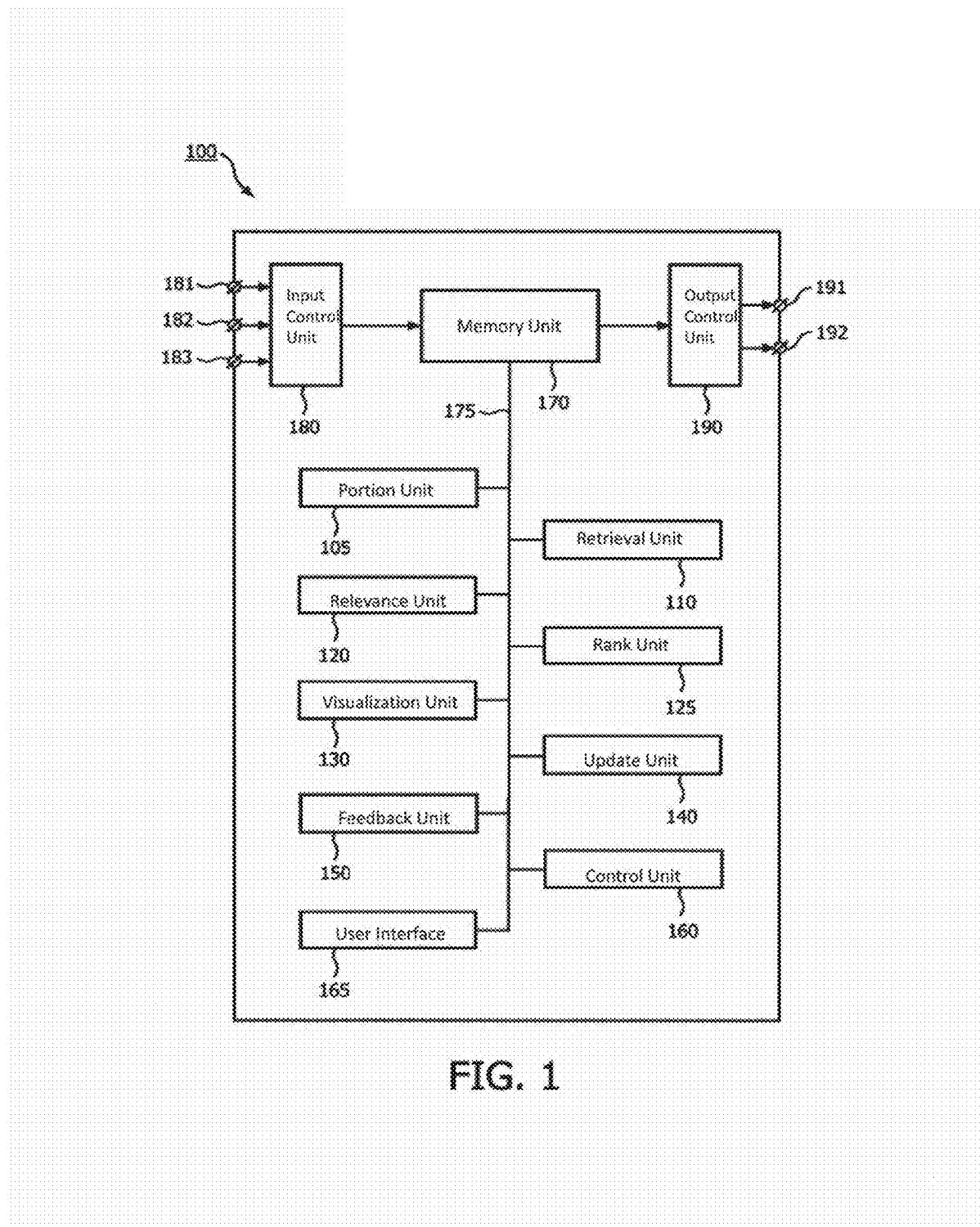
FIG. 1 shows a block diagram of an exemplary embodiment of the system.

FIG. 1 schematically shows a block diagram of an exemplary embodiment of the system 100 for retrieving an image from the storage of images, the system comprising:
- a retrieval unit 110 for retrieving an image from the storage of images, on the basis of similarity of images from the storage of images to a query image, wherein the similarity is defined by means of a similarity function;
- a relevance unit 120 for computing relevance of a first portion of the retrieved image to a respective first portion of the query image and of a second portion of the retrieved image to a respective second portion of the query image; and
- a visualization unit 130 for visualizing the relevance of the first and second portion of the retrieved image to the respective first and second portion of the query image.

The exemplary embodiment of the system 100 further comprises
- a portion unit 105 for determining the first and/or second portion of the query image;
- a rank unit 125 for determining the rank of the retrieved image, wherein the rank is determined based on the similarity of the retrieved image to the query image and/or on the relevance of the first and second portion of the retrieved image to the respective first and second portion of the query image;
- an update unit 140 for updating the similarity function on the basis of the computed values of relevance of the first and second portion of the retrieved image;

a feedback unit 150 for receiving user feedback on the relevance of the first and second portion of the retrieved image to the respective first and second portion of the query image, and wherein the update unit 140 is adapted to use the user feedback for updating the similarity function;

a control unit 160 for controlling the work of the system 100;

a user interface 165 for communication between the user and the system 100; and a memory unit 170 for storing data.

In an embodiment of the system 100, there are three input connectors 181, 182 and 183 for the incoming data. The first input connector 181 is arranged to receive data coming in from a data storage means such as, but not limited to, a hard disk, a magnetic tape, a flash memory, or an optical disk. The second input connector 182 is arranged to receive data coming in from a user input device such as, but not limited to, a mouse or a touch screen. The third input connector 183 is arranged to receive data coming in from a user input device such as a keyboard. The input connectors 181, 182 and 183 are connected to an input control unit 180.

In an embodiment of the system 100, there are two output connectors 191 and 192 for the outgoing data. The first output connector 191 is arranged to output the data to a data storage means such as a hard disk, a magnetic tape, a flash memory, or an optical disk. The second output connector 192 is arranged to output the data to a display device. The output connectors 191 and 192 receive the respective data via an output control unit 190.

A person skilled in the art will understand that there are many ways to connect input devices to the input connectors 181, 182 and 183 and the output devices to the output connectors 191 and 192 of the system 100. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 100, the system 100 comprises a memory unit 170. The system 100 is arranged to receive input data from external devices via any of the input connectors 181, 182, and 183 and to store the received input data in the memory unit 170. Loading the input data into the memory unit 170 allows quick access to relevant data portions by the units of the system 100. The input data comprises the query image. Optionally, the input data comprises image data from the storage of images. Alternatively, the storage of images may be implemented by the memory 170. Further, the input data may comprise user feedback. The memory unit 170 may be implemented by devices such as, but not limited to, a register file of a CPU, a cache memory, a Random Access Memory (RAM) chip, a Read Only Memory (ROM) chip, and/or a hard disk drive and a hard disk. The memory unit 170 may be further arranged to store the output data. The output data comprises the image or images retrieved by the retrieval unit 110, wherein the relevance of the first and second portion of the retrieved images is visualized. The output data may also comprise, for example, useful information about the updated similarity function. The memory unit 170 may be also arranged to receive data from and/or deliver data to the units of the system 100 comprising the portion unit 105, the retrieval unit 110, the relevance unit 120, the rank unit 125, the visualization unit 130, the update unit 140, the feedback unit 150, the control unit 160, and the user interface 165, via a memory bus 175. The memory unit 170 is further arranged to make the output data available to external devices via any of the output connectors 191 and 192. Storing data from the units of the system 100 in the memory unit 170 may advantageously improve performance of the units of the system 100 as well as the rate of transfer of the output data from the units of the system 100 to external devices.

In an embodiment of the system 100, the system 100 comprises a control unit 160 for controlling the system 100. The control unit 160 may be arranged to receive control data from and provide control data to the units of the system 100. For example, after computing the relevance of the first and second portion of the retrieved image to the respective first and second portion of the query image, the relevance unit 120 may be arranged to provide control data "the relevance is computed" to the control unit 160 and the control unit 160 may be arranged to provide control data "visualize the computed relevance" to the visualization unit 130. Alternatively, a control function may be implemented in another unit of the system 100.

In an embodiment of the system 100, the system 100 comprises a user interface 165 for communication between a user and the system 100. The user interface 165 may be arranged to receive a user input for downloading a query image into the memory 170 or for selecting the color and/or transparency for visualizing the relevance. Optionally, the user interface may receive a user input for selecting a mode of operation of the system such as, e.g., for registering images from the storage with the query image or for updating the similarity function. A person skilled in the art will understand that more functions may be advantageously implemented in the user interface 165 of the system 100.

In an embodiment, the system 100 is adapted for retrieving images from the storage of 2D images representing brain slices. All images are standardized, i.e. the slices are identically scaled and positioned, the position being defined, for example, by the sagittal, coronal and axial sections of the brain. The query image is standardized in the same way. Thus, no registration of storage images with the query image is necessary.

In an embodiment of the system 100, each image is divided by a regular grid into a plurality of squares of identical size. The first and second portion is defined by squares comprised in each portion. Each portion can be predefined or defined based on a user input indicating the squares to be included in the first and second portion of the query image. Since the images are standardized, the first and second portion of the retrieved image comprise the squares at the same locations as the first and second portion of the query image. Optionally, the system may be adapted to deal with a plurality of portions in the query image and in the retrieved image, the plurality of portions comprising more than two portions. A person skilled in the art will understand that other ways of defining image portions may be used, e.g. labeling pixels of a 2D image or voxels of a 3D image, defining geometrical constraints, or using contours or surfaces. The scope of the claims must not be construed as limited by the described way of defining image portions.

In an embodiment, the system 100 is adapted for retrieving a plurality of images from the storage of images and the rank unit 125 is adapted for ranking these images based on the similarity of the retrieved image to the query image. The visualization unit 130 is adapted to show a number of most relevant images.

Figure 2:
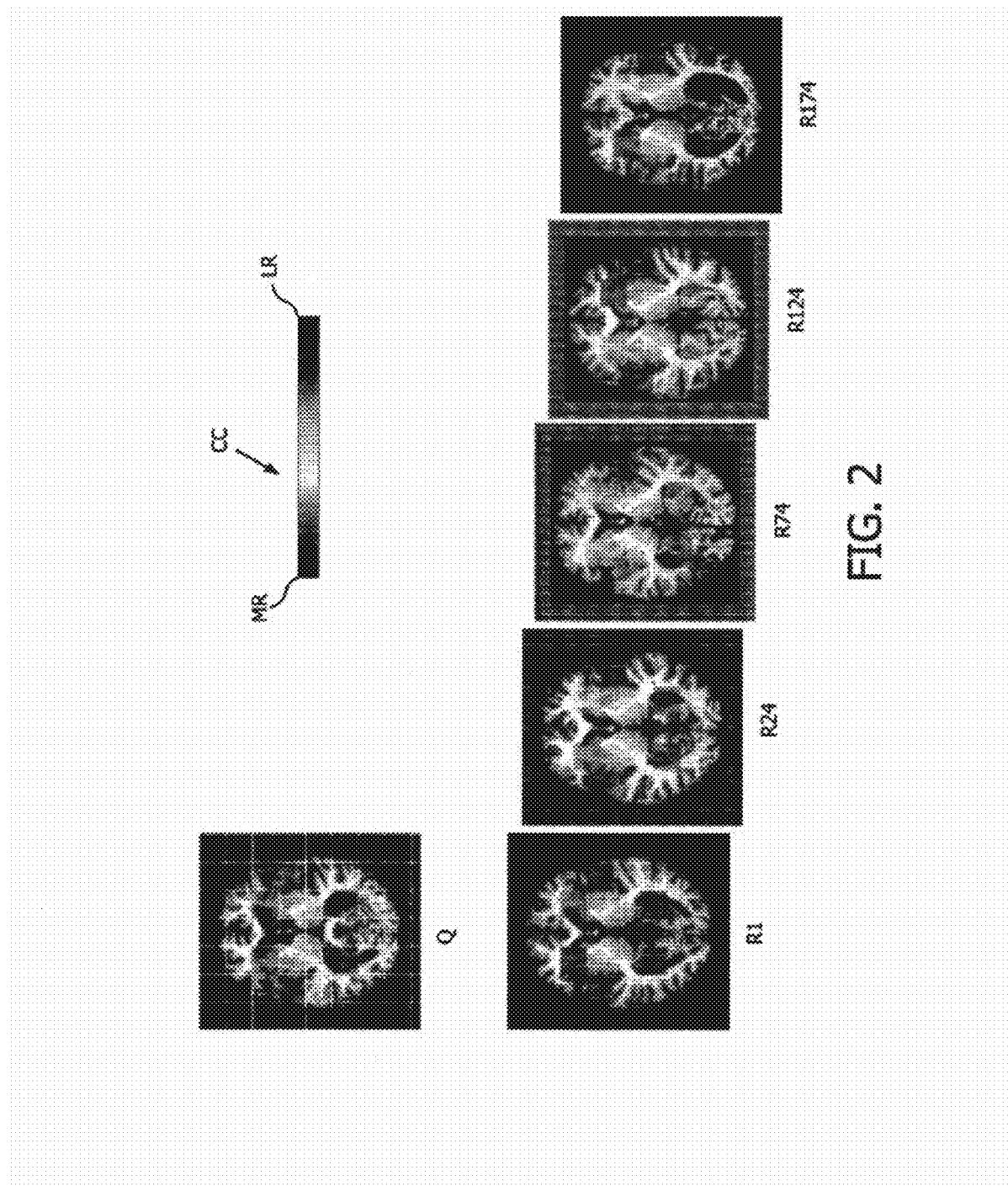
FIG. 2 shows an example of a query image and of images retrieved by the system of the invention according to an embodiment of the invention.

FIG. 2 shows an example of a query image Q and of images R1, R24, R74, R124 and R174 retrieved by the system of the invention according to an embodiment of the invention. The query image and the images in the storage of images are axial slices of the brain. The images are partitioned into squares of identical size. The query image shows a slice of the brain of a subject with Alzheimer's disease. The system is adapted for computing similarities of squares of a query image to respective squares of an image from the storage of images. The sum of said similarities is the similarity of the query image to the image from the storage. In the embodiment illustrated in FIG. 2, the sum comprises contributions from each pair of squares. Alternatively, the sum may comprise contributions from a certain set of pairs of squares.

In the embodiment illustrated in FIG. 2, six portions are selected in the query image, each portion being a square. The relevance of each portion of the retrieved image to the respective portion of the query image is equal to the similarity of said each portion of the retrieved image to said respective portion of the query image and the rank of the retrieved image is equal to the similarity of the retrieved image to the query image. The similarity of a retrieved image and the relevance of each part of the retrieved image is coded using a color. A color code map CC is illustrated in FIG. 2. The red colors at the left end MR of the color code map CC correspond to high relevance and similarity values and the blue colors at the right end LR of the color code map CC correspond to low relevance and similarity values. FIG. 2 shows five images R1, R24, R74, R124 and R174 which have ranks 1, 24, 74, 124, 174, respectively. The value of the similarity of each image of the retrieved images to the query image is represented by the color of the frame around the image of the retrieved images. The relevance of each portion of each image of the retrieved images to the respective portion of the query image is represented by the color of said portion of the image of the retrieved images. The coloring is semi-transparent to show anatomical details in the colored portions. The first image R1 is the image with the highest rank of 1. Each portion in this image is colored in a shade of red which indicates that each portion is fairly relevant to the respective portion of the query image. On the other hand, three squares of the last image R174 ranked 174 are in various shades of blue, one is yellow and two are in various shades of red.

FIG. 2 illustrates an important aspect of the system 100 of the invention. The system is adapted for indicating how similar each retrieved image is to the query image in selected areas of interest. This helps a physician in diagnosing the query image, based on the retrieved images and on the coloring of the portions of interest of the retrieved images. A person skilled in the art will understand that in some embodiments, other visual and/or audio indicators can be used in place of coloring. Examples of such indicators include, but are not limited to, brightness, frames of different colors, line widths or line types, and displayed or aural descriptions of the portions of interests in the retrieved images.

A person skilled in the art will further understand that the similarity of the retrieved image to the query image and the relevance of a portion of the retrieved image to the respective portion of the query image may be computed independently of each other. The similarity function may be purely image-based, i.e. dependent only on the image content. Alternatively the similarity function may be further based on non-image data associated with the image data. Analogously, the relevance function for computing the relevance of a portion of the retrieved image to a respective portion of the query image may be based on image data or non-image data associated with the image data. In an embodiment, the computed relevance of a portion of the retrieved image to a respective portion of the query image is used for updating the similarity function. As already mentioned in the introduction, methods of updating the similarity function based on relevance are described, for example, in the paper by Rui et al. or in the paper by Akgul et al.

In an embodiment of the system 100, the similarity function is computed based on the similarity of selected portions of interest of the query image. The remaining part of the query image is not used for computing the similarity. If the similarity function is a sum of similarity contributions, each similarity contribution being computed based on a portion of the image, the sum of similarity contributions may be a weighted sum of similarity contributions emphasizing the most important contributions to the similarity, e.g. the most important portions of the image. Optionally, the weights may be based on a user input.

A person skilled in the art will appreciate that the system 100 may be a valuable tool for assisting a physician in many aspects of her/his job. Further, although the embodiments of the system are illustrated using medical applications of the system, non-medical applications of the system are also contemplated.

Those skilled in the art will further understand that other embodiments of the system 100 are also possible. It is possible, among other things, to redefine the units of the system and to redistribute their functions. Although the described embodiments apply to medical images, other applications of the system, not related to medical applications, are also possible.

The units of the system 100 may be implemented using a processor. Normally, their functions are performed under the control of a software program product. During execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 3:
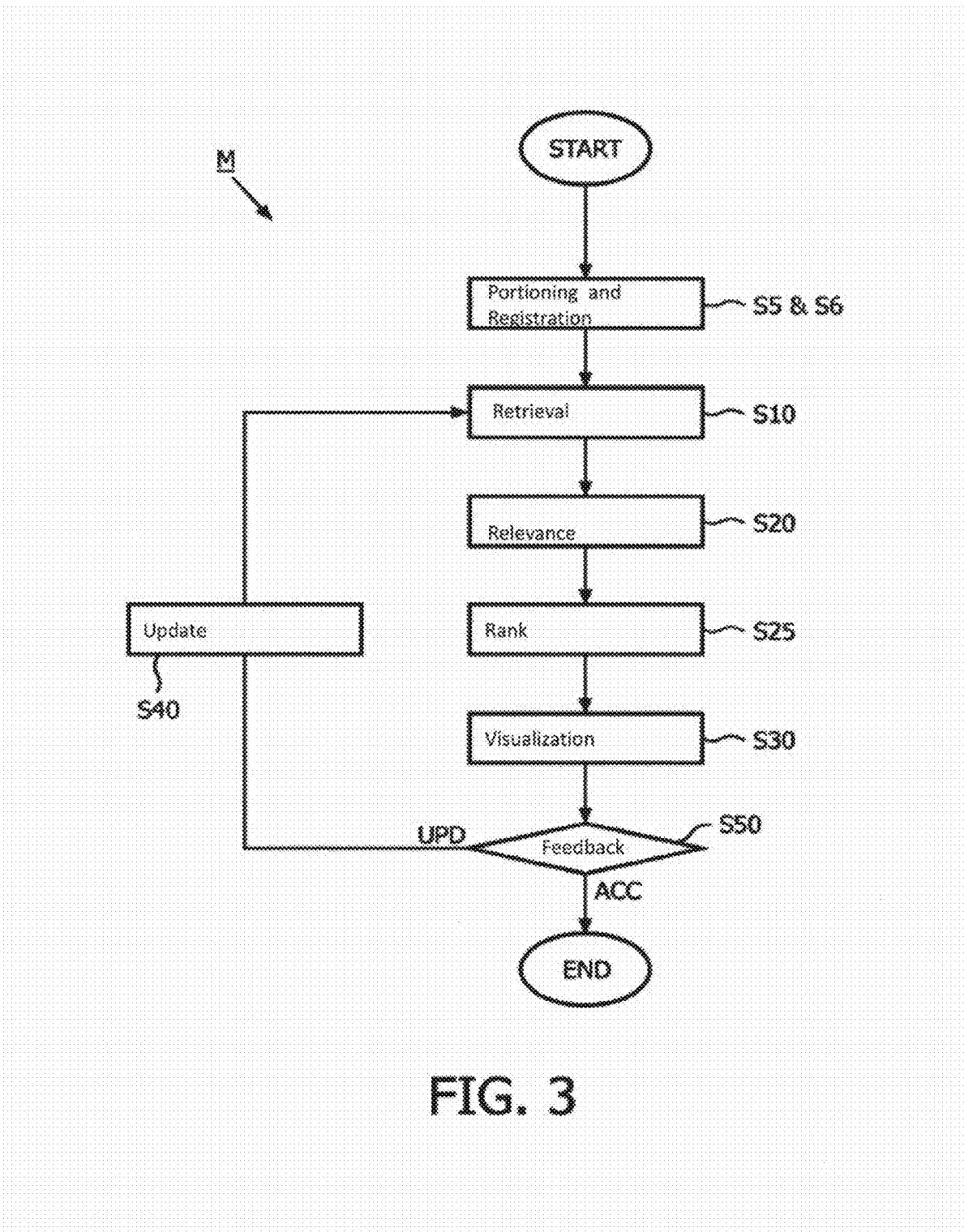
FIG. 3 shows a flowchart of exemplary implementations of the method.

An exemplary flowchart of the method M of retrieving an image from the storage of images is schematically shown in FIG. 3. The method M begins with a portion step S05 for determining a first and/or second portion of the query image. After the portion step S05 or concurrently with this step, the method M continues to a registration step S06 for registering a query image with images from the storage of images. After the portion and registration steps, S05 & S06, the method M continues to a retrieval step S10 for retrieving an image from the storage of images, on the basis of similarity of images from the storage of images to a query image. The similarity is defined and computed by means of a similarity function. After the retrieval step S10, the method M continues to a relevance step S20 for computing relevance of a first portion of the retrieved image to the first portion of the query image and of a second portion of the retrieved image to the second portion of the query image. After the relevance step S20, the method M continues to a rank step S25 for determining the rank of the retrieved image, wherein the rank is determined based on the similarity of the retrieved image to the query image and/or on the relevance of the first and second portion of the retrieved image to the respective first and second portion of the query image. After the rank step S25, the method M continues to a visualization step S30 for visualizing the relevance of the first and second portion of the retrieved image to the respective first and second portion of the query image. The relevance may be visualized by displaying the value of the relevance of each portion of the retrieved image, the value being visually associated with the respective portion. Preferably, each portion of the retrieved image can be colored according to a color code for coding relevance values with colors. After the visualization step S30, the method M continues to the feedback step S50 for receiving user feedback on the relevance of the first and second portion of the retrieved image to the respective first and second portion of the query image. If the user accepts the computed relevance by providing an ACC input, the method terminates. Otherwise, the user provides an UPD input and the method M then continues to an update step S40 for updating the similarity function on the basis of the computed values of relevance of the first and second portion of the retrieved image. Optionally, in the feedback step S50, the user may evaluate computed values of relevance according to an evaluation scheme. The evaluation scheme may be based on an evaluation scale which may be two-valued (e.g. good and wrong), three valued (e.g. good, neutral, wrong), etc. The user evaluation is included in the user input UPD. After evaluating computed values of relevance, the method M continues to the update step S40 for updating the similarity function on the basis of the computed values of relevance of the first and second portion of the retrieved image and, optionally, uses also the user evaluation, included in the user feedback UPD, for updating the similarity function. After the update step S40, the method returns to the retrieval step S10 and follows the steps S20, S25, S30 and S50.

A person skilled in the art may change the order of some steps or perform some steps concurrently using threading models, multi-processor systems or multiple processes without departing from the concept as intended by the present invention. Optionally, two or more steps of the method M may be combined into one step. Optionally, a step of the method M may be split into a plurality of steps.

Figure 4:
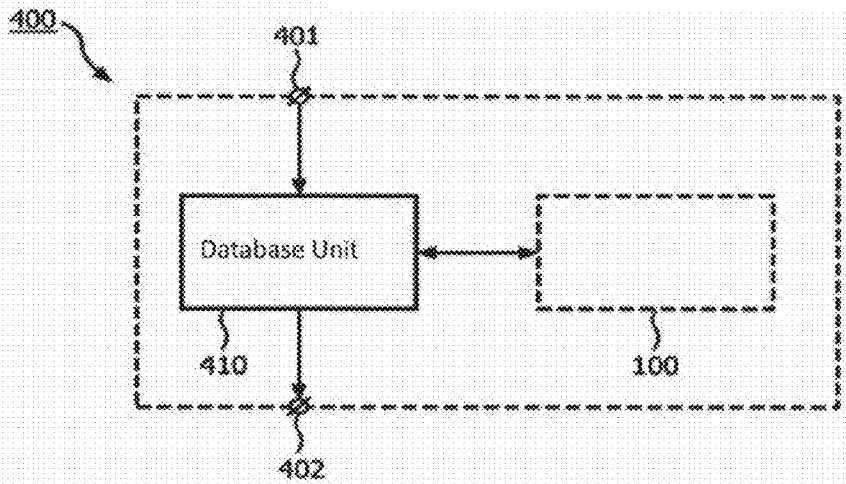
FIG. 4 schematically shows an exemplary embodiment of the database system.

FIG. 4 schematically shows an exemplary embodiment of the database system 400 employing the system 100 of the invention, said database system 400 comprising a database unit 410 connected via an internal connection to the system 100, an external input connector 401, and an external output connector 402. This arrangement advantageously increases the capabilities of the database system 400, providing said database system 400 with advantageous capabilities of the system 100.

Figure 5:
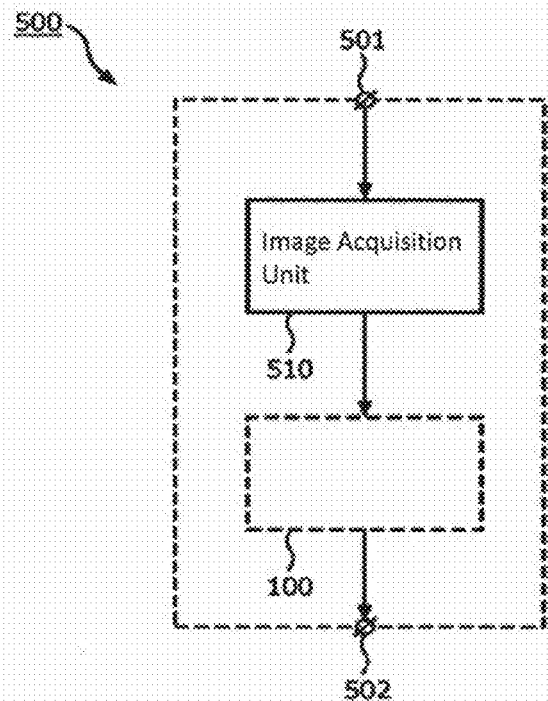
FIG. 5 schematically shows an exemplary embodiment of the image acquisition apparatus.

FIG. 5 schematically shows an exemplary embodiment of the image acquisition apparatus 500 employing the system 100 of the invention, said image acquisition apparatus 500 comprising an image acquisition unit 510 connected via an internal connection with the system 100, an input connector 501, and an output connector 502. This arrangement advantageously increases the capabilities of the image acquisition apparatus 500, providing said image acquisition apparatus 500 with advantageous capabilities of the system 100.

Figure 6:
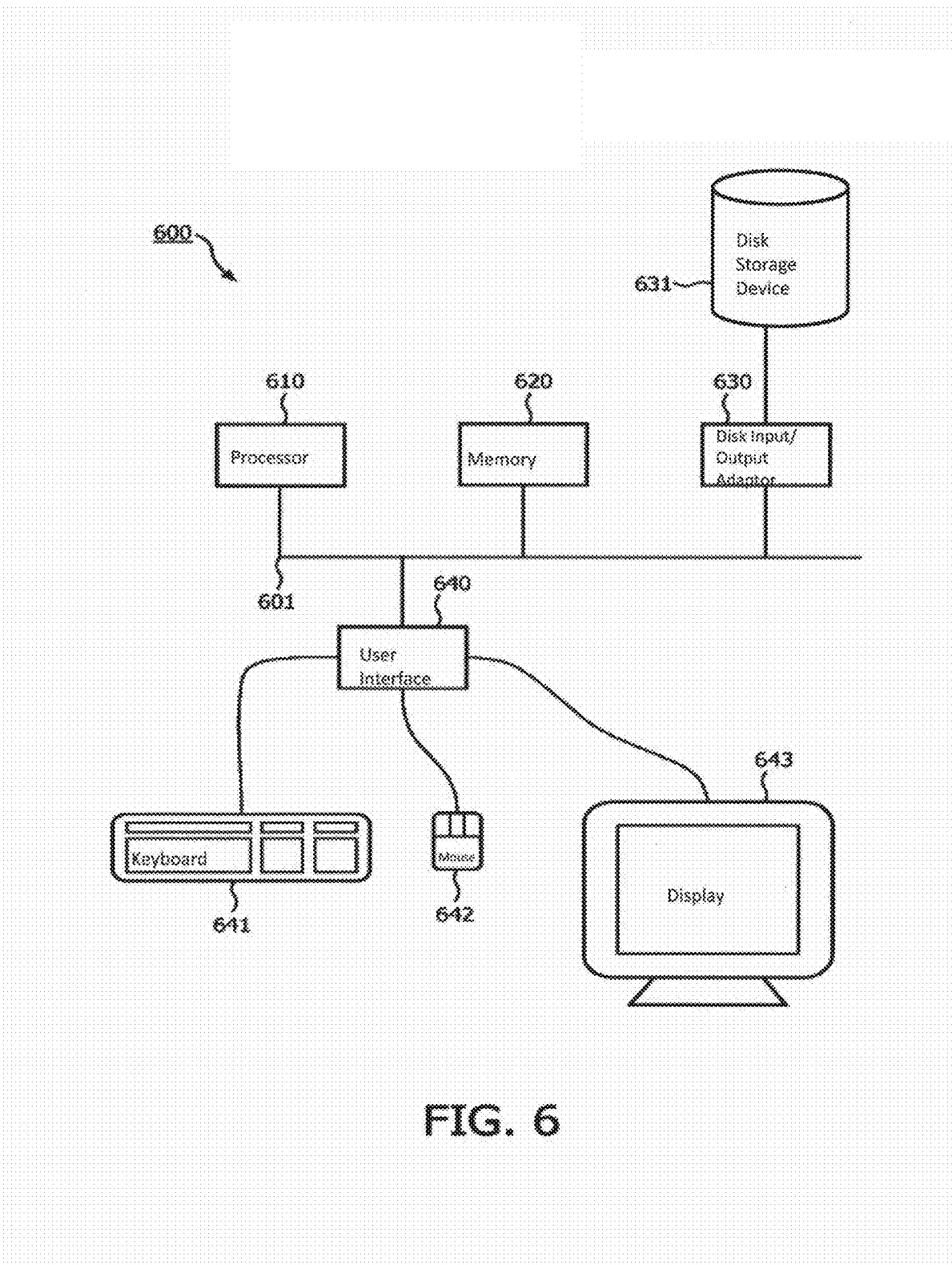
FIG. 6 schematically shows an exemplary embodiment of the workstation.

FIG. 6 schematically shows an exemplary embodiment of the workstation 600. The workstation comprises a system bus 601. A processor 610, a memory 620, a disk input/output (I/O) adapter 630, and a user interface (UI) 640 are operatively connected to the system bus 601. A disk storage device 631 is operatively coupled to the disk I/O adapter 630. A keyboard 641, a mouse 642, and a display 643 are operatively coupled to the UI 640. The system 100 of the invention, implemented as a computer program, is stored in the disk storage device 631. The workstation 600 is arranged to load the program and input data into memory 620 and execute the program on the processor 610. The user can input information to the workstation 600, using the keyboard 641 and/or the mouse 642. The workstation is arranged to output information to the display device 643 and/or to the disk 631. A person skilled in the art will understand that there are numerous other embodiments of the workstation 600 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same record of hardware or software. The usage of the words first, second, third, etc., does not indicate any ordering. These words are to be interpreted as names.

The invention claimed is:

1. A system for assisting diagnoses, the system comprising:
a memory which stores a plurality of reference images which have been standardized to have a common scale and position, the reference images being made up of one of pixels and voxels;
one or more processors programmed to:
receive a query image depicting anatomy of a patient to be diagnosed, the query image being made up of one of pixels and voxels;
standardize the query image to the common scale and position,
divide the query image and the reference images with a common grid to define corresponding portions of the query image and the reference images, each portion including a plurality of at least one of pixels and voxels,
receiving an input selecting a plurality of the corresponding, portions,
compute a degree of similarity of each of the selected corresponding portions of the query image with the selected corresponding portions of the reference images,
based on the computed degrees of similarity, select relevant ones of the reference images,
control a display device to display the query image and the selected relevant ones of the reference images with the selected corresponding portions of the selected relevant ones of the reference images marked to indicate the computed degree of similarity with the selected corresponding portion of the query image.

2. The system as claimed in claim 1, wherein the query image is a brain slice image and the reference images are brain slice images of patients diagnosed with Alzheimer's disease such that the displayed query image and the displayed reference images with corresponding portions colorized to indicate similarity are indicative of whether the query image is indicative of Alzheimer's disease and a progression of the Alzheimer's disease.

3. The system as claimed in claim 1, wherein the one or more processors is further programmed to:

control the display device to color code the corresponding portions of the displayed reference images to indicate the computed degree of similarity with semi-transparent colors.

4. The system as claimed in claim 1, wherein the one or more processors is further programmed to:
segment the query image.

5. The system as claimed in claim 1, further comprising:
a user input device which receives user feedback on the computed relevance of the selected corresponding portions of the displayed reference images to the selected corresponding portions of the query image, and wherein the one or mere processors is further programmed to:
update the computed degree of similarity based on the received user feedback.

6. The system as claimed in claim 1, wherein the one or more processors is programmed to select the reference images to be displayed by:
weighting the computed degrees of similarity of the selected corresponding portions of each of the reference images to the selected corresponding portions of the query image the relative weighting being based on a location of each selected portion in the query image; and
adding the weighted computed degrees of similarity of the corresponding portions of each of the reference images.

7. The system as claimed in claim 1, further including:
a diagnostic imager which generates the query image and the reference images;
wherein the memory stores the reference images in conjunction with medical diagnostic information.

8. A method of retrieving reference images from an image memory, the method comprising, with one or more processor;
(a) receiving a query image, the query image and the reference images have corresponding portions;
(b) selecting a plurality of the corresponding portions of the query image and the reference images;
(c) registering the query image with the reference images;
(d) retrieving one of the reference images from the image memory;
(e) comparing the selected corresponding portions of the query image and the one of the reference images using a similarity function to determine a degree of similarity score of each of the corresponding portions;
(f) weighting the degree of similarity scores based on positions of the selected corresponding portions such that similarity of at least one of the selected corresponding portions is weighted more heavily than at least one other of the selected corresponding portions;
(g) combining the weighted degree of similarity scores to generate a relevance value for the retrieved one of the reference images such that the relevance values are positionally weighted;
(h) repeating steps (d)-(g) for a plurality of the reference images;
(i) ranking the reference images based on the relevance values;
(j) selecting a plural number of the reference images based on the ranking;
(k) controlling a display device to display the query image and the selected plural number of reference images with the corresponding portions of the query image of each of displayed reference images denoted, such that as viewer can compare the corresponding portions of the query image and the displayed reference images.

9. A non-transitory computer readable medium carrying a computer program for controlling one or more processors to perform the method as claimed in claim 8.

10. The method as claimed in claim 8, further including, with the one or more processors:
controlling the display device to indicate the degree of similarity score of each of the selected portions of each of the displayed reference image using semi-transparent color coding.

11. The method as claimed in claim 8, further including:
with the one or more processors, segmenting the query image and the reference images.

12. The method as claimed in claim 10, further including, with the one or more processors:
standardizing the reference images and the query image to a common size and position;
dividing each standardized reference image and each query image with a common grid to define the plurality of corresponding portions.

13. The method as claimed in claim 10, further including:
with a user input device, inputting feedback on the similarity of the corresponding portions of the displayed query image and the displayed reference images.

14. The method as claimed in claim 8, further including:
wherein the reference images are anatomical diagnostic brain images of patients diagnosed with Alzheimer's disease and the query image is a brain image of a patient.

* * * * *